United States Patent
Donze et al.

(10) Patent No.: US 9,303,177 B2
(45) Date of Patent: Apr. 5, 2016

(54) ODOR CONTROL BULK MATERIAL COVER

(71) Applicant: LSC ENVIRONMENTAL PRODUCTS, LLC, Apalachin, NY (US)

(72) Inventors: Joseph W. Donze, Chicopee, MA (US); Joel E. Lanz, Apalachin, NY (US); Luke Emmett Cody, Syracuse, NY (US)

(73) Assignee: LSC ENVIRONMENTAL PRODUCTS, LLC, Apalachin, NY (US)

( * ) Notice: Subject to any disclaimer, the term of this patent is extended or adjusted under 35 U.S.C. 154(b) by 0 days.

(21) Appl. No.: 14/759,694

(22) PCT Filed: Jan. 9, 2014

(86) PCT No.: PCT/US2014/010823
§ 371 (c)(1),
(2) Date: Jul. 8, 2015

(87) PCT Pub. No.: WO2014/110227
PCT Pub. Date: Jul. 17, 2014

(65) Prior Publication Data
US 2015/0344717 A1  Dec. 3, 2015

Related U.S. Application Data

(60) Provisional application No. 61/751,526, filed on Jan. 11, 2013.

(51) Int. Cl.
| | | |
|---|---|---|
| *C09D 103/02* | (2006.01) | |
| *C09D 101/08* | (2006.01) | |
| *C09D 7/12* | (2006.01) | |
| *A61L 2/00* | (2006.01) | |
| *A61L 9/00* | (2006.01) | |
| *C08K 3/34* | (2006.01) | |
| *C08K 5/13* | (2006.01) | |
| *C08K 11/00* | (2006.01) | |

(52) U.S. Cl.
CPC ............... *C09D 103/02* (2013.01); *A61L 2/00* (2013.01); *A61L 9/00* (2013.01); *C09D 7/1216* (2013.01); *C09D 7/1233* (2013.01); *C09D 101/08* (2013.01); *C08K 3/346* (2013.01); *C08K 5/13* (2013.01); *C08K 11/00* (2013.01)

(58) Field of Classification Search
None
See application file for complete search history.

(56) References Cited

U.S. PATENT DOCUMENTS

| | | | | |
|---|---|---|---|---|
| 4,269,723 A | | 5/1981 | Barford et al. | |
| 5,183,655 A | * | 2/1993 | Stanislowski | A01K 1/0152 119/171 |
| 5,275,508 A | * | 1/1994 | Hansen | B09B 1/004 405/129.9 |
| 5,352,444 A | * | 10/1994 | Cox | A61L 9/01 424/617 |
| 5,516,830 A | * | 5/1996 | Nachtman | B01F 5/106 428/2 |
| 5,582,573 A | | 12/1996 | Weszely | |
| 6,019,963 A | | 2/2000 | Kling et al. | |
| 6,287,550 B1 | | 9/2001 | Trinh et al. | |
| 7,544,243 B2 | * | 6/2009 | Hansen | B09B 1/004 106/644 |
| 8,030,391 B2 | * | 10/2011 | Petri | C08F 2/24 524/110 |
| 2005/0271609 A1 | | 12/2005 | Fei et al. | |
| 2006/0276366 A1 | | 12/2006 | Deljosevic et al. | |
| 2011/0274634 A1 | | 11/2011 | Rieth et al. | |
| 2012/0040880 A1 | | 2/2012 | Rieth et al. | |

FOREIGN PATENT DOCUMENTS

WO  2011/134074 A1  11/2011

OTHER PUBLICATIONS

International Search Report and Written Opinion for International Application No. PCT/US2014/010823, mailed Apr. 1, 2014.

* cited by examiner

*Primary Examiner* — Melvin C Mayes
*Assistant Examiner* — Colette Nguyen
(74) *Attorney, Agent, or Firm* — Heslin Rothenberg Farley & Mesiti P.C.

(57) ABSTRACT

An odor suppressing cover material for a bulk material pile and method for applying the cover material are disclosed. The cover composition includes at least 50 weight percent water; 1 to 50 weight percent of a bentonite clay; 0.1% to 5% cellulosic water dispersible polymer or starch; and 0.02% to 1% of a mixture containing at least some lipid essential oil and at least some ethoxylated alkylphenol. The cover composition may additionally and optionally contain Portland cement, colorant and fibers.

17 Claims, No Drawings

US 9,303,177 B2

ODOR CONTROL BULK MATERIAL COVER

CROSS REFERENCE TO RELATED APPLICATIONS

This application is a national stage filing under section 371 of International Application No. PCT/US2014/010823, filed on Jan. 9, 2014, and published on Jul. 17, 2014 as WO 2014/110227, which claims priority to U.S. provisional application 61/751,526, filed Jan. 11, 2013. The entire disclosures of said applications are hereby incorporated by reference herein.

FIELD OF THE INVENTION

This invention relates to protective coverings for bulk material piles, for example, for waste piles. Particularly, the invention relates to sprayable cover materials for odiferous waste piles.

BACKGROUND OF THE INVENTION

During the processing of waste, for instance sewage sludge, manure etc, the waste is concentrated into piles for storage and for transportation. When waste of this sort is concentrated into piles, it is often desirable to cover the waste piles to minimize the emission of odor. Additionally, as recycling has become more common across the United States, diluents to the organic waste stream have been diverted, and the waste stream for landfills has become more concentrated with putrid and putrifiable materials and therefore more offensive. As a result, a need has developed for a cover that resists odor permeation for time periods on the order of 24 hours or more. Such a cover would also be useful, for example, for covering all sorts of organic waste—such as sewage sludge, animal waste, food waste and municipal waste—in a truck during transport, as all of these utilities require odor suppression for periods of several hours.

Spray-on coatings have been developed to provide an effective cover to landfill and waste piles. These are primarily intended to physically stabilise the waste (e.g. prevent blowing litter, block access by disease vectors and act as a fire retardant) and only incidentally may suppress odors. They include the coatings described in U.S. Pat. Nos. 5,161,915; 5,275,508; 5,385,429; 5,525,009; and 7,544,243 (the disclosures of which are incorporated by reference here in their entirety), which are marketed under the registered trademark POSI-SHELL by LSC Environmental Products, LLC of Apalachin, N.Y. These cover materials typically comprise a mixture of water, mineral binder (such as cement kiln dust, "CKD," or similar materials), and fibers (both cellulose and synthetic) that can be sprayed onto a waste pile and allowed to set to provide a cover that is effective to stabilise the waste. Other known cover materials, for example, those described in U.S. Pat. Nos. 5,082,500 and 5,516,830, are primarily fiber based. Such prior cover materials typically stabilize the waste, but the gaseous components of the waste quickly permeate the cover and escape, so that odors are not effectively suppressed when the waste is itself offensively odiferous.

One technique described in the art for addressing the odor problem is to spray an aqueous aerosol of essential oil and nonyl phenoxy polyethoxy ethanol into the air above the source of the odor. While this is said to be effective, it requires sophisticated equipment and expertise to generate a continuous aerosol, and there is little residual effect—within a short period after the application is terminated, the odor returns. In another approach the odor-suppressant is specifically designed for mixing into the odor generating material. This approach suffers from the drawback that that the odor-suppressing composition must come into intimate contact with the odor-generating material throughout its entire mass.

Aspects of the present invention overcome these and other limitations of the prior art and provide an effective odor-barrier bulk material pile cover that can be easily applied and maintained and that provides more effective odor suppression over longer times.

SUMMARY OF THE INVENTION

The present invention provides an improved cover material and a method for applying the cover material to a pile. In one aspect, the invention relates to a cover for mitigating odor from a bulk material pile comprising: (a) at least about 50 weight percent water; (b) about 1 to about 50 weight percent of a bentonite clay; (c) 0.1% to 5% cellulosic water dispersible polymer; and (d) 0.02% to 1% of a mixture containing at least some lipid essential oil and at least some ethoxylated alkylphenol. The composition may additionally comprise fiber and/or coloring agent.

In another aspect the invention relate to a concentrate for preparing the aqueous cover composition of the foregoing paragraph. The concentrate comprises: (a) about 50 to about 99 weight percent of bentonite clay; (b) 0.5% to 25% cellulosic water dispersible polymer; and (c) 0.1% to 10% of a mixture containing a lipid essential oil and an ethoxylated alkylphenol. The composition may additionally comprise fiber and/or coloring agent.

In another aspect, the invention relates to a method of providing a cover to a bulk material pile. The method comprises providing the cover composition described above, and applying the compositors onto the bulk material pile.

DETAILED DESCRIPTION OF THE INVENTION

The invention provides compositions and methods for covers for odiferous bulk material, such as municipal waste, animal waste and sewage sludge. The compositions for use as covers comprise five elements: water, bentonite clay, water dispersive polymer or starch, essential oil and ethoxylated alkylphenol. The compositions may optionally contain colorant, and fibers.

According to aspects of the invention, the water may be landfill leachate, industrial wastewater, or combinations thereof, or any other source of water that is readily available. Untreated pond water and water that contains amounts of contaminants that would make it unsuitable as drinking water may be used as the source of the liquid. Though a weight percent water of about 90% (that is, prior to or during application to the pile) may be used, in some aspects, the weight percent of liquid may be 70%-95% or 80%-95%. The amounts discussed herein are intended to be within 5% of the value stated unless higher precision is expressly indicated. For example "80%" or "about 80%" means 80±4%.

The source of both substantivity and bulk is bentonite clay. Bentonite is an absorbent aluminium phyllosilicate, consisting mostly of montmorillonite. There are different types of bentonite, each named after the respective dominant element, such as potassium (K), sodium (Na), calcium (Ca), and aluminium (Al). For industrial purposes, two main classes of bentonite exist: sodium and calcium bentonites. A preferred bentonite is sodium bentonite, or its principal constituent, sodium montmorillonite.

The polymer binder may be a water dispersible cellulose-derived polymer. All water-dispersible cellulosic polymers are envisioned, but those that are cold-water dispersible (i.e.

under 40° C.) are preferred. Suitable polymers include methylcellulose, ethyl methyl cellulose, hydroxyethyl cellulose (HEC), hydroxypropyl cellulose, hydroxyethyl methyl cellulose, hydroxypropyl methyl cellulose (HEC), hydroxypropyl cellulose, hydroxyethyl methyl cellulose, hydroyypropyl methyl cellulose (HPMC), ethyl hydroxyethyl cellulose and carboxymethyl cellulose. In some embodiments the polymer is chosen from hydroxypropyl methyl cellulose (HPMC), hydroxyethylcellulose (HEC) and mixtures thereof. In some embodiments the polymer is hydroxyethyl methyl cellulose. The polymer may comprise about 0.1 weight percent to about 5 weight percent of the aqueous slurry, prior to or during application. In one aspect, the polymer may be about 0.25 weight percent to about 5 weight percent, or about 0.5 weight percent to about 2 weight percent of the material. In some embodiments, the polymer comprises 0.25 to 3.0 weight percent of the slurry. As an adhesive agent in place of—or in addition to—the cellulosic polymer, one may include wheat starch, for instance, pregelatinized wheat starch. The content of pregelatinized wheat starch may vary from about 0.1 weight percent to about 2 weight percent, typically about 0.2 weight percent to about 1.4 weight percent.

An essential oil is a concentrated hydrophobic liquid containing volatile aroma compounds from plants. Essential oils are also known as volatile oils and ethereal oils or simply as the "oil of" the plant from which they were extracted, such as oil of clove. An oil is "essential" in the sense that it carries a distinctive scent, or essence, of the plant. Examples of essential oils include orange, lemon, lime, field mint (*Mentha arvenis*), peppermint, spearmint, wintergreen, menthol, camphor, anise, allspice, clove, almond, vanilla, celery, nutmeg, cassia (*Cinnamomum cassia*), ginger, sage, buchu (*Agathosma* sp.), cedarwood, eucalyptus, May chang (*Litsea cubeba*), sassafras, rosewood, sandalwood, pine, balsam, juniper, tea tree (*Melaleuca* sp.) and patchouli. Citrus oils (e.g. orange, lemon, lime) and mint oils (e.g. field mint (*Mentha arvensis*) peppermint, spearmint, wintergreen, menthol) are readily available, effective and relatively inexpensive, which recommend them for application in the compositions described herein. In certain embodiments of the compositions of the invention, tea tree, eucalyptus and pine oils may be absent.

Ethoxylated alkylphenols are well known in the surfactant and emulsifier art. Two common classes are the nonoxynols and the octoxynols, many embodiments of which are commercially available from Rhodia/Solvay as their IGEPAL® series of emulsifiers. The IGEPAL® CO series of nonyl phenoxy polyethoxy ethanols are preferred, and octoxynol-9 is particularly preferred.

As discussed above, the cover material may also include a coloring agent. A coloring agent may be added to the compositions listed in Table 1 to provide the desired opacity or to provide an aesthetically pleasing shade of color to the composition. In one aspect, the coloring agent may comprise any conventional coloring agent, for example, a mortar dye, for instance, TRUE-TONE® mortar dye provided by Davis Color Corporation, may be added if desired, though other coloring agents may be used. In one aspect, from about 0.01 weight percent to about 1.0 weight percent coloring agent may be added to the composition, for example, from about 0.02 to about 0.5 weight percent coloring agent may be added.

The cover may also contain an optional fiber component. The fibers may include cellulose and/or plastic fibers. Sources of cellulose fibers include shredded newspaper, mixed types of shredded paper and/or shredded wood fiber. These cellulose fiber constituents may be used separately or in various combinations. Newspapers, magazines, phone books, etc. may be shredded into particles, preferably less than one-half inch in any dimension. In order to ensure proper liquid content in the total mixture, the moisture content of shredded paper may be adjusted, commonly to around 6 percent by weight. Shredded wood fibers may also be used as a constituent provided that the wood fibers are finely shredded. The shredded wood fiber must be in a string or hair-like shape such as fine excelsior. Wood chips are generally not satisfactory for use as the cellulose fiber constituent.

The constituents which may be used as plastic fibers include high density polyethylene, polyvinyl chloride, polypropylene, polyethylene terephthalate, as well as other types of plastics, shredded into thin hair-like fibers. Optimally the hair-like fibers are between one-quarter to one-half inch in length. Polyethylene terephthalate fibers, such as LSC P-100 fiber, which are manufactured from recycled products such as plastic soda containers, have been found suitable.

Other optional constituents that can be added to the compositions of the invention include Portland cement, cement kiln dust, fly ash, or stone dust, or any combination of these. In many embodiments, the composition will be free of zeolites, cyclodextrins, urease inhibitors, antimicrobials, borates, boric acid and metal salts other than alkali and alkaline earth metal salts. By "free of" it is meant that the named constituent is substantially absent; it may be present in trace, non-functional amounts as an impurity, typically less than 0.1% by weight.

The composition may be applied in any thickness desired, as long as the thickness is sufficient to cover the surface of the substrate without leaving gaps. It has been found that a thickness of ⅓ to ½ inch (3 mm to 13 mm) provides adequate coverage without wasting material, although thicker coverage may be used. Generally, an increase in duration of effect accompanies an increase in thickness.

Details of these aspects of the invention, as well as further aspects of the invention, will become more readily apparent upon review of the following detailed description and the accompanying claims. In order to facilitate the description of aspects of the present invention, the following discussion will primarily refer to the present invention as it is applied to cover animal waste or sewage sludge. It will be apparent to those of skill in the art, that the cover composition and application process described may also be applied for other uses, including both waste and non-waste uses.

In one aspect, the invention relates to a composition as shown in Table 1.

TABLE 1

Typical Content of Cover Composition Prior to Application According to One Aspect of the Invention

| Constituent | Quantity (weight percent) |
|---|---|
| water | at least 50 |
| bentonite | 11 to 50 |
| polymer or starch | 0.1 to 5 |
| essential oil | 0.005 to 0.6 |
| ethoxylated alkylphenol | 0.005 to 0.6 |

The essential oil and the ethoxylated alkylphenol can be added together, as a mixture, in which the ratio of essential oil to ethoxylated alkylphenol can be from 2:1 to 1:2 and the mixture constitutes 0.02% to 1% by weight of the composition.

A representative composition of one embodiment of the invention is shown in Table 2.

TABLE 2

Content of Cover Composition Prior to Application
According to One Embodiment of the Invention

| Constituent | Quantity (weight percent) |
| --- | --- |
| water | 90-92 |
| bentonite | 8-9 |
| polymer or starch | 0.1-0.5 |
| essential oil | 0.01-0.04 |
| ethoxylated alkylphenol | 0.01-0.04 |

Other embodiments comprise compositions including fiber and/or colorant. The fiber may be present in 5 to 10% by weight of the total composition. A water-conditioning agent, for example soda ash ($Na_2CO_3$), may also be added to the compositions described above to improve the efficiency of the wetting of the bentonite. This property of soda ash may be particularly useful when hard water is used as the source of liquid for the composition. Soda ash may be introduced at 2 to 10 weight percent of the bentonite. For example, the soda ash, if present, may comprise from about 0.05 weight percent to about 4 weight percent of the entire composition.

According to a further aspect, the invention also relates to a concentrate that is used to prepare the aqueous composition described above. The concentrate is provided as a dry mix to be added to water to make the slurry described above. The concentrate comprises, in its simplest form, bentonite, the water-dispersable polymer and/or starch and the essential oil/ethoxylated alkylphenol mixture. Bentonite may be provided in the form of PSM-200 setting agent provided by Landfill Service Corporation. PSM-200 setting agent typically contains finely ground natural bentonite clay (for example, which can pass through a minus 200 sieve); a synthetic polymer, for example, less than 10% synthetic polymer by weight; pregelatinized wheat starch and soda ash. The concentrate is prepared by mechanically mixing the bentonite and, if not already present, the water-dispersable polymer, then adsorbing the essential oil/ethoxylated alkylphenol mixture onto the bentonite. This is most conveniently accomplished by providing the essential oil/ethoxylated alkylphenol mixture in a liquid form as a concentrated solution or suspension. If the solution is sprayed onto the solid bentonite at a rate of about 100-200 mL per square meter, optimally about 150 mL/$m^2$, it will adsorb and quickly form a free-flowing solid concentrate. The concentrate may then be packaged and subsequently mixed with water, optionally on the job site.

The concentrate may be a dry powder comprising (a) from 50 to 99 weight percent of a bentonite clay; (b) from 0.5% to 25% cellulosic water dispersible polymer; and (c) from 0.1% to 10% of a mixture containing a lipid essential oil and an ethoxylated alkylphenol. It may additionally comprise from 0.1% to 5% of a colorant and/or from 0.5% to 5% of a fiber. In an embodiment, the concentrate may comprise (a) from 90 to 99 weight percent of a bentonite clay; (b) from 0.5% to 5% of a cellulosic water dispersible polymer; and (c) from 0.1% to 1% of a mixture containing a lipid essential oil and an ethoxylated alkylphenol. The concentrate may be provided in bulk or in the form of unit packages of 50 or 100 pounds.

Mixing is accomplished in any convenient fashion. In one aspect, the water and bentonite in the form of PSM-200 setting agent with essential oil/ethoxylated alkylphenol adsorbed thereon may be mixed first. The mixture may be mixed continuously with a mixing agitator while the ingredients are added. If desired, the fibers and or coloring agent may be added at this point. Typically, the mixture of liquid, bentonite, and optional additional ingredients may be allowed to thicken to form a viscid slurry that resembles a cake batter or milk shake. The mixing time necessary to yield a mixture with the proper consistency may vary depending upon the percentage of each constituent added to the mixture. Once mixed, the composition may continue to be agitated, for example, slowly agitated, for instance, by means of a commercial mixing device, such as a Landfill Service Corporation PSA 2000 Applicator mixer, or its equivalent. If the composition requires transport to the point of application, the mixture may be agitated during transport.

When the mixture is properly agitated, a spray applicator allows the mixture to be sprayed onto the substrate surface using a motion similar to spray painting. The mixture is sprayed in such a manner that a uniform layer approximately one-eighth to one-half, preferably a quarter, of an inch thick exists.

Some experiments were carried out to explore aspects of the invention. Panels of 5, 6 or 7 adult volunteers were used to assess the offensiveness of test batches of sewage sludge coated with a 0.5 cm cover layer of various formulations. In these tests, the human waste was contained in a Petri dish with a cone inverted over the dish, and the test subject inhaled just above the orifice of the cone. This is a very demanding test. Under such conditions, human subjects can detect odors that when released under natural conditions outdoors, might not be perceived as offensive. In a first experiment, the water, bentonite and polymer components of the composition (133:10:0.6) were applied as the cover layer to sewage sludge. In this test, the panel detected no odor suppression. In a second experiment, Portland cement was added to the panel (133:10:0.6:10). Odor was suppressed for about 4 hours but then began to break through. In a third experiment, a mixture of essential oil and ethoxylated alkylphenol in water (133:0.13) was sprayed on top. No odor suppression was noted. In a fourth experiment, the water, essential oil, ethoxylated alkylphenol bentonite and polymer components of the composition (133:10:0.6) were mixed together and applied as in the first experiment. Odor was initially suppressed, but fully returned within four hours. In a fifth experiment, water, bentonite, and an odor suppressant not of the invention (133:10:0.14) were sprayed on top. No odor suppression was noted. The odor suppressant not of the invention was in the form of proprietary granules sold by Odor Control Company of Scottsdale, Ariz. It is believed to be essential oils of plants in the order Coniferae adsorbed on a mineral carrier other than bentonite and without ethoxylated alkylphenol. In a sixth experiment, the water, polymer and bentonite to which the mixture of essential oil and ethoxylated alkylphenol had been preadsorbed according to an embodiment of the invention (133:10:0.6:0.1) were applied; odor suppression was effective out to six hours. In a seventh experiment, to the water, polymer, bentonite/mixture of essential oil and ethoxylated alkylphenol components was added 10 parts of Portland cement (133:10:0.1:10), and the composition was applied to the sludge; odor suppression was effective out to 24 hours.

Finally, two full-scale tests were run. In the first test, on a truckload of cow manure, a cover composition according to an embodiment of the invention (133:10:0.6:01; water, bentonite, polymer and mixture of essential oil and ethoxylated alkylphenol) was applied at a rate of 6.7 liters per square meter. The odor was suppressed for a period sufficient to transport the manure to a remote site. In the second test, the same composition was applied at the same rate (6.7 liters per square meter) to a 28 square meter surface of a trailer load of sewage sludge. The originally vile odor was completely suppressed for a period sufficient to transport the sludge to a remote site.

The invention claimed is:

1. A cover composition for mitigating odor from a bulk material pile comprising:
   (a) at least about 50 weight percent water;
   (b) about 1 to about 50 weight percent of a bentonite clay;
   (c) 0.1% to 5% cellulosic water dispersible polymer or starch;
   (d) 0.02% to 1% of a mixture containing lipid essential oil and ethoxylated alkylphenol.

2. A cover composition according to claim 1, wherein the water comprises about 75 to about 95 weight percent water.

3. A cover composition according to claim 1, which comprises about 5 to about 25 weight percent of bentonite.

4. A cover composition according to claim 3, wherein the weight percent of bentonite is from 5 to 12 weight percent.

5. A cover composition according to claim 1, wherein the water dispersible polymer or starch constitutes from 0.1 to 0.5 by weight of the cover composition.

6. A composition according to claim 5, wherein the water dispersible polymer or starch comprises one or more of methylcellulose, ethyl methyl cellulose, hydroxyethyl cellulose (HEC), hydroxypropyl cellulose, hydroxyethyl methyl cellulose, hydroxypropyl methyl cellulose (HPMC), ethyl hydroxyethyl cellulose and carboxymethyl cellulose.

7. A composition according to claim 5, wherein the water dispersible polymer or starch comprises pregelatinized wheat starch.

8. A cover composition according to claim 1, wherein the ratio of essential oil to ethoxylated alkylphenol is from 2:1 to 1:2 and the mixture constitutes 0.02% to 1% by weight of the composition.

9. A cover composition according to claim 8, wherein the ethoxylated alkylphenol is nonyl phenoxy polyethoxy ethanol.

10. The composition as recited in claim 1, wherein the lipid essential oil is one or more of a citrus, mint or vanilla oil and the ethoxylated alkylphenol is nonyl phenoxy polyethoxy ethanol.

11. A cover composition according, to claim 1 wherein the bentonite clay is sodium montmorillonite.

12. A cover composition according to claim 1, wherein the composition further comprises a coloring agent.

13. A concentrate composition for preparing an aqueous bulk material cover composition comprising:
   (a) 50 to 99 weight percent of a bentonite clay;
   (b) 0.5% to 25% cellulosic water dispersible polymer;
   (c) 0.1% to 10% of a mixture containing a lipid essential oil and an ethoxylated alkylphenol.

14. The concentrate according to claim 13 additionally comprising one or both of the following:
   (d) 0.1% to 5% of a colorant;
   (e) 0.5% to 5% of a fiber.

15. A concentrate composition according to claim 13 comprising;
   (a) 90 to 99 weight percent of a bentonite clay;
   (b) 0.5% to 5% cellulosic water dispersible polymer;
   (c) 0.1% to 1% of a mixture containing a lipid essential oil and an ethoxylated alkylphenol.

16. A method of providing a cover to a bulk material pile, the method comprising:
   providing the cover composition recited in claim 1; and
   applying the composition onto the bulk material pile.

17. The method as recited in claim 16, wherein said cover has a thickness of about 0.3 to 1.3 cm (⅛ inch to about ½ inch).

* * * * *